United States Patent
Mansi et al.

(10) Patent No.: US 11,515,030 B2
(45) Date of Patent: Nov. 29, 2022

(54) SYSTEM AND METHOD FOR ARTIFICIAL AGENT BASED COGNITIVE OPERATING ROOMS

(71) Applicant: Siemens Healthcare GmbH, Erlangen (DE)

(72) Inventors: Tommaso Mansi, Plainsboro, NJ (US); Ankur Kapoor, Plainsboro, NJ (US); Thomas Pheiffer, Philadelphia, PA (US); Vincent Ordy, Amiens (FR); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1017 days.

(21) Appl. No.: 16/310,565

(22) PCT Filed: Jun. 23, 2017

(86) PCT No.: PCT/EP2017/065560
§ 371 (c)(1),
(2) Date: Dec. 17, 2018

(87) PCT Pub. No.: WO2017/220788
PCT Pub. Date: Dec. 28, 2017

(65) Prior Publication Data
US 2019/0333626 A1    Oct. 31, 2019

Related U.S. Application Data

(60) Provisional application No. 62/353,907, filed on Jun. 23, 2016.

(51) Int. Cl.
G09B 23/28 (2006.01)
G16H 30/40 (2018.01)
(Continued)

(52) U.S. Cl.
CPC ........... *G16H 30/40* (2018.01); *A61B 5/7267* (2013.01); *A61B 5/742* (2013.01); *A61B 5/7405* (2013.01);
(Continued)

(58) Field of Classification Search
CPC ............ A61B 2034/258; A61B 5/7267; A61B 5/7405; A61B 5/742; A61B 5/746;
(Continued)

(56) References Cited

U.S. PATENT DOCUMENTS 7,822,291 B2    10/2010    Guetter et al.
9,084,531 B2     7/2015    Chen et al.
(Continued)

OTHER PUBLICATIONS

International Search Report dated Sep. 29, 2017 in corresponding International Patent Application No. PCT/EP2017/065560.
(Continued)

*Primary Examiner* — Anh V La (57) ABSTRACT

An artificial agent based cognitive operating room system and a method thereof providing automated assistance for a surgical procedure are disclosed. Data related to the surgical procedure from multiple data sources is fused based on a current context. The data includes medical images of a patient acquired using one or more medical imaging modalities. Real-time quantification of patient measurements based on the data from the multiple data sources is performed based on the current context. Short-term predictions in the surgical procedure are forecasted based on the current context, the fused data, and the real-time quantification of the patient measurements. Suggestions for next steps in the surgical procedure and relevant information in the fused data are determined based on the current context and the short-
(Continued)

term predictions. The suggestions for the next steps and the relevant information in the fused data are presented to an operator.

26 Claims, 6 Drawing Sheets

(51) Int. Cl.

| | | |
|---|---|---|
| *A61B 34/10* | (2016.01) | |
| *A61B 34/00* | (2016.01) | |
| *G06T 7/30* | (2017.01) | |
| *G16H 40/63* | (2018.01) | |
| *A61B 5/00* | (2006.01) | |
| *G08B 7/06* | (2006.01) | |
| *G09B 19/00* | (2006.01) | |
| *G06T 7/11* | (2017.01) | |
| *G06T 7/20* | (2017.01) | |

(52) U.S. Cl.
CPC .............. *A61B 5/746* (2013.01); *A61B 34/10* (2016.02); *A61B 34/25* (2016.02); *G06T 7/30* (2017.01); *G08B 7/06* (2013.01); *G09B 19/003* (2013.01); *G16H 40/63* (2018.01); *A61B 2034/104* (2016.02); *A61B 2034/105* (2016.02); *A61B 2034/107* (2016.02); *A61B 2034/252* (2016.02); *A61B 2034/258* (2016.02); *G06T 7/11* (2017.01); *G06T 7/20* (2013.01); *G06T 2207/20081* (2013.01); *G06T 2207/30004* (2013.01)

(58) Field of Classification Search
CPC ... A61B 34/10; A61B 34/25; A61B 2034/104; A61B 2034/105; A61B 2034/107; A61B 2034/252; G06T 7/11; G06T 7/20; G06T 2207/20081; G06T 2207/30004; G06T 7/30; G16H 20/40; G16H 70/20; G16H 30/20; G16H 50/20; G16H 30/40; G16H 40/63; G08B 7/06; G09B 19/003
USPC ...... 434/262, 267; 340/573.1; 600/410, 424, 600/425, 408
See application file for complete search history.

(56) References Cited

U.S. PATENT DOCUMENTS

| | | | |
|---|---|---|---|
| 9,349,098 B1 | 5/2016 | Ionson et al. | |
| 10,653,368 B1* | 5/2020 | McNair | A61B 5/021 |
| 2003/0190954 A1* | 10/2003 | Sitrick | A63F 13/655 |
| | | | 348/E5.058 |
| 2008/0234322 A1* | 9/2008 | Syroid | A61K 31/02 |
| | | | 514/731 |
| 2013/0211230 A1* | 8/2013 | Sperling | A61B 8/565 |
| | | | 600/425 |
| 2014/0088990 A1* | 3/2014 | Nawana | G16H 50/20 |
| | | | 705/2 |
| 2014/0108983 A1* | 4/2014 | William R | |
| 2015/0364022 A1* | 12/2015 | Dyell | A61B 5/746 |
| | | | 340/573.1 |
| 2016/0067007 A1 | 3/2016 | Piron et al. | |
| 2017/0330075 A1 | 11/2017 | Tuysuzoglu et al. | |
| 2017/0337682 A1 | 11/2017 | Liao et al. | |

OTHER PUBLICATIONS

Makary, et al.; "Medical error—the third leading cause of death in the US." BMJ 353 (2016): i2139.
Lalys, et al. "Surgical process modelling: a review." International journal of computer assisted radiology and surgery 9, No. 3 (2014): 495-511.
[Sensis] http://usa.healthcare.siemens.com/angio/workplaces/sensis; retrieved from the Internet.
[Buzz] https://www.brainlab.com/en/surgery-products/overview-platform-products/buzz-digital-or/; retrieved from the internet.
Ghesu, et al.; "Towards Intelligent Image Parsing with Deep Reinforcement Learning", MICCAI; 2016.
Neumann, et al.; "A self-taught artificial agent for multi-physics computational model personalization." Medical image analysis (2016).
Zettinig, et al. "Data-driven estimation of cardiac electrical diffusivity from 12-lead ECG signals." Medical image analysis 18.8 (2014): 1361-1376.
Voigt, et al.; "Robust Live Tracking of Mitral Valve Annulus for Minimally-Invasive Intervention Guidance." In International Conference on Medical Image Computing and Computer-Assisted Intervention, Springer International Publishing, 2015.
El-Zehiry, et al.; "A System and Method for the Live Landmark Tracking in Ultrasound Sequences", invention disclosure; 2015.
Santoro, et al.; "One-shot Learning with Memory-Augmented Neural Networks." arXiv preprint arXiv:1605.06065 (2016).

* cited by examiner

SYSTEM AND METHOD FOR ARTIFICIAL AGENT BASED COGNITIVE OPERATING ROOMS

This application claims the benefit of U.S. Provisional Application No. 62/353,907, filed Jun. 23, 2016, the disclosure of which is herein incorporated by reference in its entirety.

BACKGROUND OF THE INVENTION

The present invention relates to an artificial agent for providing artificial intelligence based operating room support, and more particularly to a system and method for providing an intelligent artificial agent that supports the clinical workflow around surgical procedures.

With the boom of medical technologies and increasingly complex therapies, the operating room (OR) is becoming an extremely complex environment, with several actors and multiple, real-time but asynchronous information streams (e.g., live imaging, physiological data, patient history, medical body of knowledge, etc.) to mentally integrate. As a result, the main operator (e.g., surgeon, interventional cardiologist, etc.) may be overloaded with information from multiple sources while at the same time performing complex tasks. This is true for the entire patient care workflow, from treatment preparation (planning, patient preparation, etc.) to the treatment itself, to follow up care.

BRIEF SUMMARY OF THE INVENTION

The present invention provides an artificial agent based cognitive operating room system and method thereof. The present inventors have recognized that there is a need to centralize data acquired from multiple sources in the operating room (OR) in a consistent, time-synchronized fashion, present the data in a unified way to the OR actors, and assist the operators in their tasks with an intelligent system that understands the current situation and can predict what will happen next for context-aware support and medical reasoning. Such a system would not only simplify the OR environment, thus increasing safety and efficacy, but also increase throughput through automation with intelligent imaging and medical systems, and smoothen the learning curve of the operators.

Embodiments of the present invention provide an intelligent, ubiquitous artificial agent that supports the clinical workflow around surgical procedures. The artificial agent supports a next generation cognitive OR in which an intelligent system automatically integrates information from multiple sources and selectively presents the information to the operators based on the surgical procedure, the stage of the intervention, the user, etc. The intelligent system is context aware and reasons based on the various data streams and prior knowledge, such as patient medical history, operator experience and preferences, and medical knowledge like guidelines, recommendations, clinical trial results, etc.

In one embodiment of the present invention, data related to the surgical procedure from multiple data sources is fused based on a current context. The data includes medical images of a patient acquired using one or more medical imaging modalities. Real-time quantification of patient measurements based on the data from the multiple data sources is performed based on the current context. Short-term predictions in the surgical procedure are forecasted based on the current context, the fused data, and the real-time quantification of the patient measurements. Suggestions for next steps in the surgical procedure and relevant information in the fused data are determined based on the current context and the short-term predictions. The suggestions for the next steps and the relevant information in the fused data are presented to an operator.

These and other advantages of the invention will be apparent to those of ordinary skill in the art by reference to the following detailed description and the accompanying drawings.

DETAILED DESCRIPTION

The present invention relates to an artificial agent based cognitive operating room system and method thereof. Embodiments of the present invention provide a system and method in which an intelligent artificial agent provides support for the clinical workflow of procedures based on medical images and other data streams. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or a remote computer system.

Embodiments of the present invention provide an intelligent, ubiquitous artificial agent that supports the clinical workflow around surgical procedures, including planning, patient preparation, intervention, monitoring, and/or follow-up. The intelligent artificial agent supports a next generation cognitive operating room (OR) in which an intelligent system automatically integrates data from multiple sources and selectively presents the data to operators based on the surgical procedure, the stage of the intervention, the user, etc. According to an advantageous aspect of the present invention, the intelligent artificial agent is context aware and performs reasoning and/or prediction based on the data streams and prior knowledge, such as patient medical history, operator experience and preferences, and medical body of knowledge (e.g., guidelines, recommendations, clinical trial results, etc.).

Figure 1:
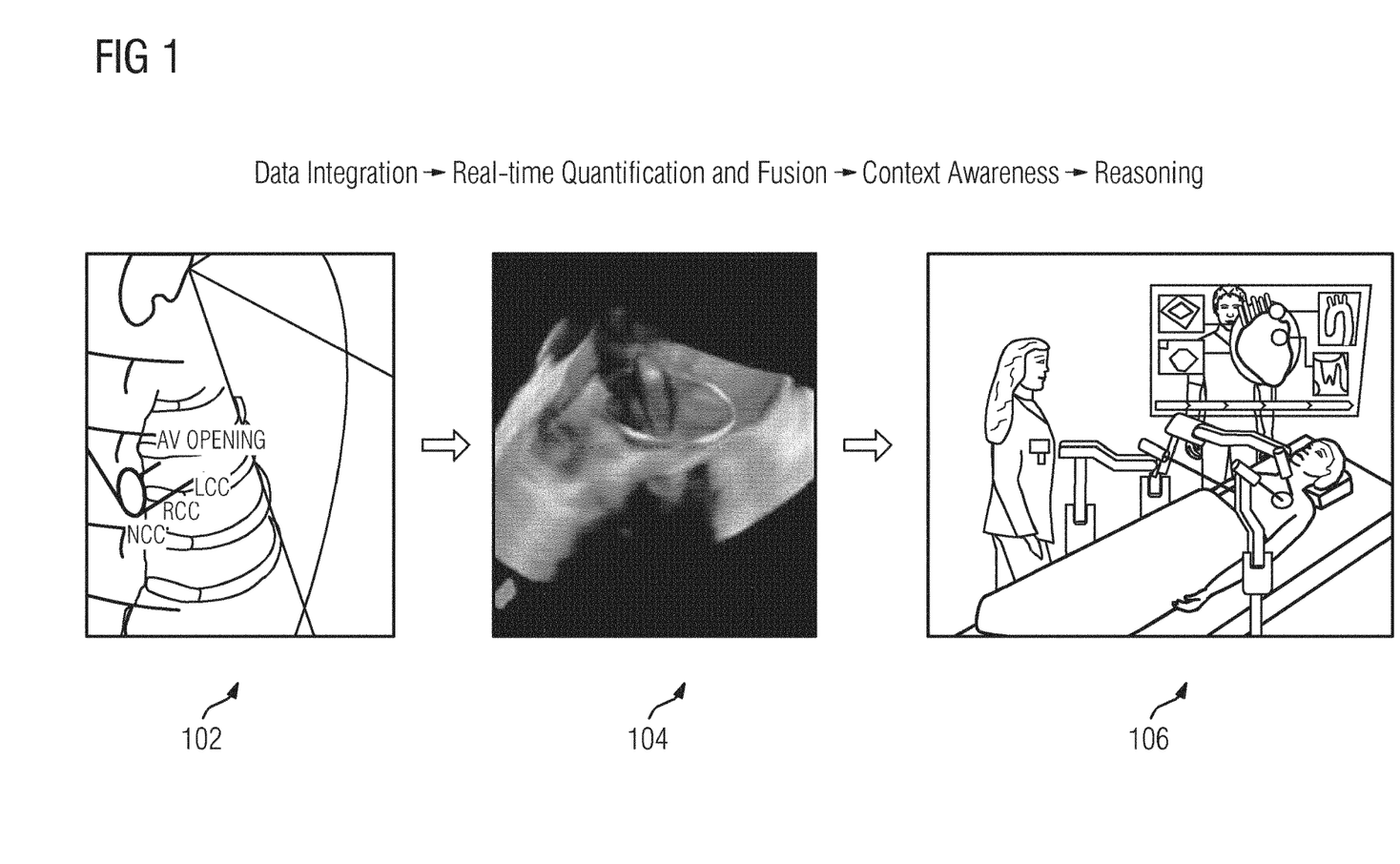
FIG. 1 illustrates a high-level workflow of an intelligent artificial agent based cognitive operating room (OR) system according to an embodiment of the present invention.

FIG. 1 illustrates a high-level workflow of an intelligent artificial agent based cognitive OR system according to an embodiment of the present invention. As shown in FIG. 1, the artificial agent based cognitive OR system performs data integration (shown in image 102), in which OR "signals" or data streams (e.g., medical images from medical imaging scanners, real-time quantification and fusion (shown in image 104), context-awareness, and reasoning to automatically generate short term predictions to anticipate upcoming events, suggest next steps, and reduce risks. The results of the context-aware reasoning performed by the system are provided in real-time to operators in the OR, as shown in image 106.

In an advantageous embodiment of the present invention, real-time data streams are integrated into a common data model and representation system (time-synchronized but asynchronous). The data streams can include medical imaging devices, cameras, physiological information, etc. Information of the integrated data streams is then fused based on the current context, for example using multi-modality image and data fusion algorithms. The information of the integrated data streams is quantified based on the current context, for example using segmentation and tracking algorithms and/or live measurements. Analyzing and predicting next phases are performed based on the fused information, the quantification results, computational and statistical models, and background knowledge (e.g., medical body of knowledge, patient history, etc.). Next steps are proposed and alerts are raised based on the current context background information, and short-term predictions. The intelligent artificial agent interacts with the operator(s) using ubiquitous human-machine interactions and context-aware data presentation. In a possible embodiment, several artificial agents can work together, collaboratively or competitively, for distributed support.

Figure 2:
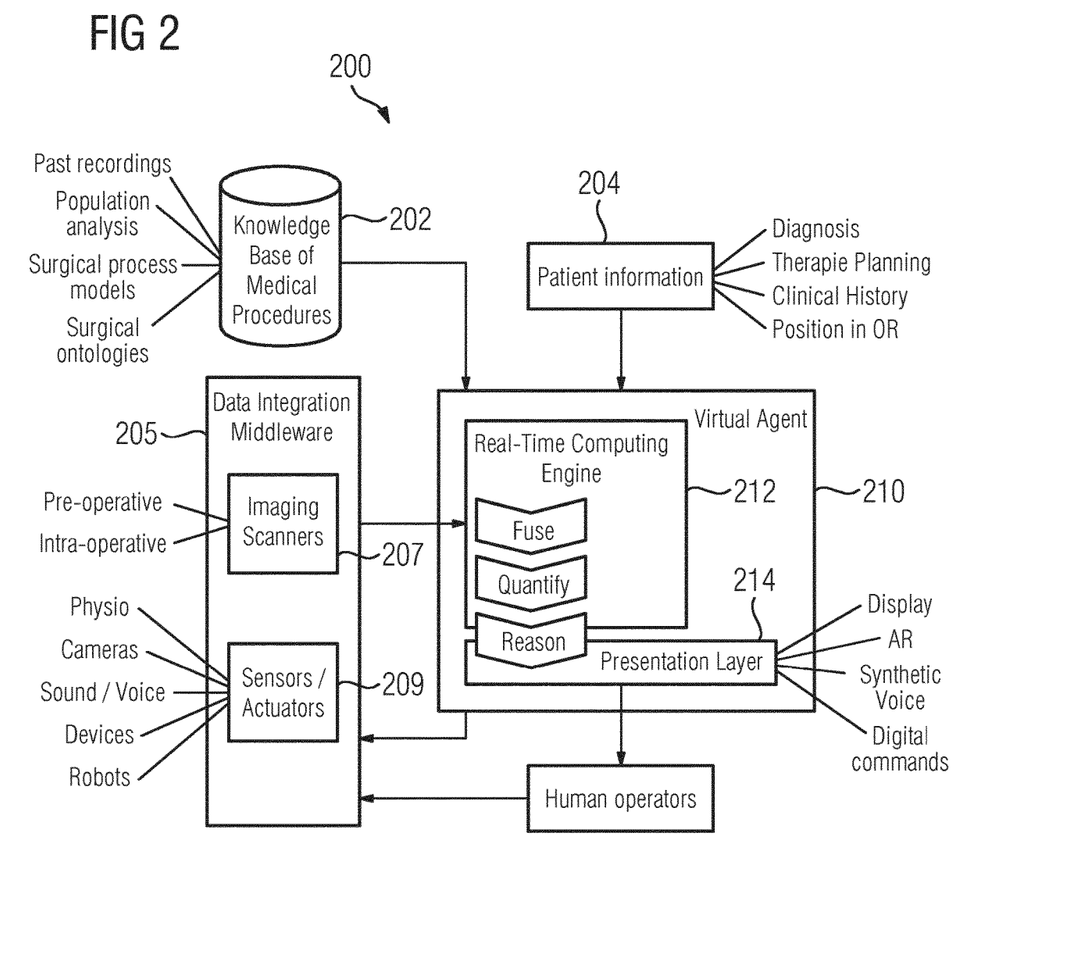
FIG. 2 a cognitive OR system for providing automated assistance for surgery or therapy according to an embodiment of the present invention.

FIG. 2 a cognitive OR system 200 for providing automated assistance for surgery or therapy according to an embodiment of the present invention. The system 200 includes data integration middleware 205 and a virtual agent 210. The data integration middleware 205 integrates data from various data sources, including real-time data streams, into a common data model and representation system. The data sources can include medical imaging scanners 207 and other sensors/actuators 209. The medical imaging scanners 207 can include any medical imaging modalities, such as computed tomography (CT), magnetic resonance imaging (MRI), ultrasound, DynaCT, X-ray, laparoscopic, endoscopic, etc. The medical imaging scanners can be used to acquire pre-operative medical images of the patient (e.g., CT, MRI, etc.) and intra-operative medical images of the patient (e.g., ultrasound, X-ray angiography, laparoscopic, endoscopic, etc.) The intraoperative medical images may be received as a real-time data stream. The sensors/actuators 209 may include physiological sensors that acquire physiological measurements of the patient (e.g., ECG, blood pressure, temperature, heart rate, etc.), cameras (3D or 2D cameras), sound/voice sensors and/or actuators, devices (e.g., medical devices, probes, etc.), and/or robots (e.g., robotic systems with actuators that are controllable by the virtual agent 210). Data from the sensors/actuators 209, such as clinical measurements and camera images, may be received as real-time data streams. The data integration middleware 205 is implemented on a computer system and stores the data acquired from the various data sources (medical images, clinical measurements, etc.) in order to centralize the data from the various sources. The data integration middleware 105 also time-synchronizes the data in the real-time data streams. The data integration middleware 105 can be implemented using an information technology (IT) infrastructure that centralizes and synchronizes the data streams.

The virtual agent 210 is a computer-based intelligent artificial agent that uses artificial intelligence to intelligently fuse data, quantify patient measurements from the data, reason, and present information to provide context aware guidance during a surgical intervention. The virtual agent 210 can also perform actions such as automatically deciding to fuse or quantify some aspects in an image or autonomously controlling devices in the OR. The virtual agent 210 is implemented on one or more computers or processors by executing computer program instructions (code) loaded into memory. The virtual agent 210 determines a current context for the surgical intervention based on the data integrated by the data integration middleware 205 (e.g., medical images, physiological measurements, etc.) patient information 204, and information from a knowledge base of medical procedures 202, and autonomously performs the data fusion, quantification, reasoning, and presentation based on the current context. In one embodiment, the virtual agent 210 can be implemented on a local computer device in the OR. In this case, the virtual agent 210 and the data integration middleware 205 may be run on separate computer devices or on the same computer device. In another embodiment, the virtual agent 210 can be implemented on one or more remote devices, such as in a cloud-based computing system.

The virtual agent 210 includes a real-time computing engine 212 and an adaptive presentation layer 214. The real-time computing engine 212 performs real-time data fusion, quantification, and reasoning based on the data integrated by the data integration middleware 205, patient information 204, and information the knowledge base of medical procedures 202. Additional details regarding the real-time fusion, quantification, and reasoning are described in greater detail below. The presentation layer 214 provides a seamless interface with the user(s)/operator(s) by showing or telling only the relevant information at any specific time of the surgical procedure. The presentation layer 214 can interact with the user(s) and/or OR environment in various ways. For example, the presentation layer 214 can provide information, such as guidance for next steps of the surgical procedure, alerts, etc., by displaying information on a display device, using an augmented reality (AR) view, speaking information using a synthetic voice, and/or using digital commands to control other devices in the OR. Additional details regarding the presentation of information by the presentation layer 214 are described below.

Patient information 204, such as a patient diagnosis, therapy planning information, clinical history, and the patient position in the OR is input to the virtual agent 210. Patient information 204 may be stored in a patient information database. For example, patient information 204 may be stored on a medical information system, such as a picture archiving and communication system (PACS). The virtual agent 210 can also retrieve information, such as past recordings, population analysis, surgical process models, surgical ontologies, medical guidelines and recommendations, and clinical trial results, from a knowledge base of medical procedures 202.

Figure 3:
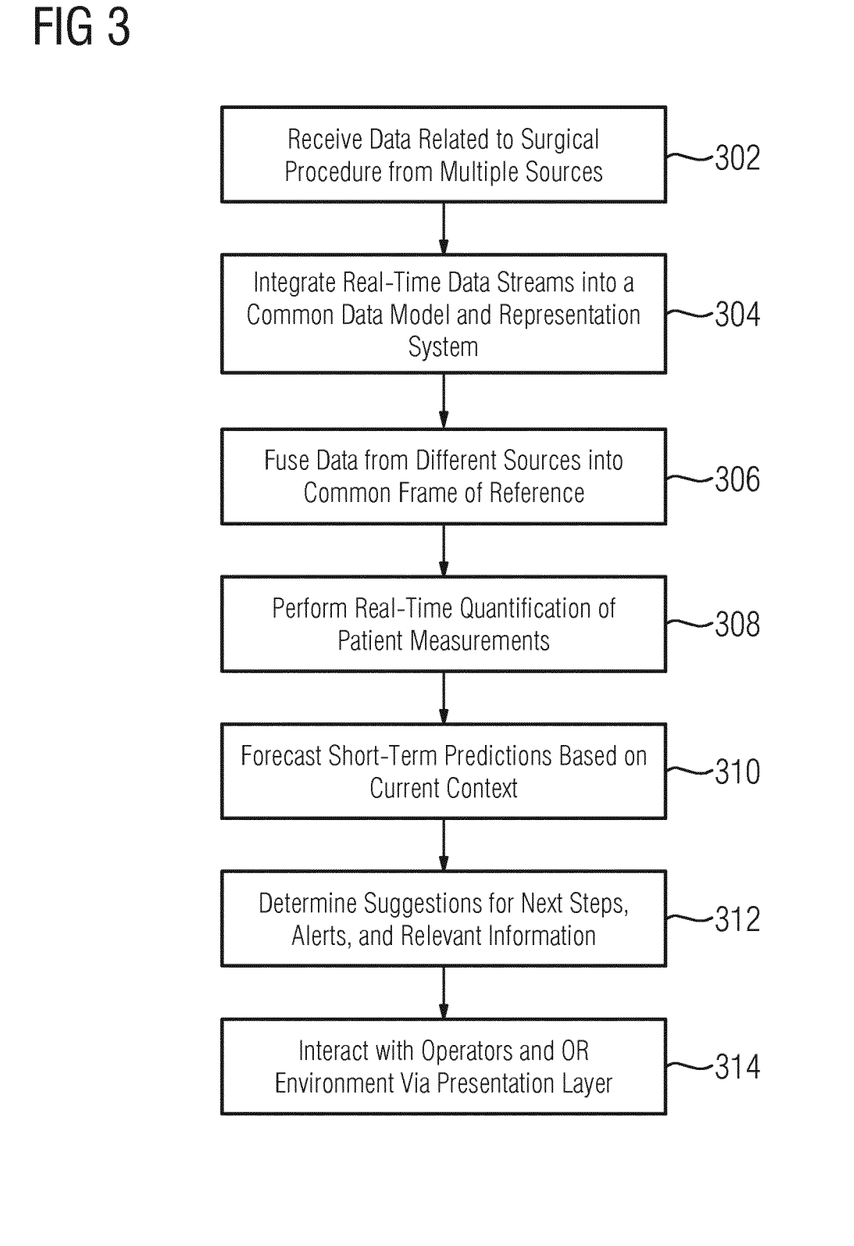
FIG. 3 illustrates a method for providing automated assistance for a surgical procedure using the system of FIG. 2 according to an embodiment of the present invention.

FIG. 3 illustrates a method for providing automated assistance for a surgical procedure using the system of FIG. 2 according to an embodiment of the present invention. As illustrated in FIG. 3, at step 302, data related to the surgical procedure is received from multiple data sources. As describe above, the data can include medical images (pre-operative and intra-operative) acquired using medical imaging scanners 207 for various medical imaging modalities, physiological measurements, camera images (e.g., RGB-D images), and other sensor/actuator data. Some of the data (e.g., intra-operative images, physiological measurements, camera images) can be received in real-time data streams. At step 304, the data integration middleware 205 integrates the data into a common data model and representation system. This results in the data from the various sources being centralized and time-synchronized.

At step 306, the data from the different data sources is fused in a common frame of reference. This data fusion is performed by the real-time computing engine 212 of the virtual agent 210. Although in the method of FIG. 3 the data fusion is performed at step 306 and the real-time quantification is performed at step 308, it is also possible that the data fusion and real-time quantification steps be performed in parallel.

Images are fused together using image registration technologies. While standard image registration techniques apply, in an advantageous embodiment artificial intelligence is used to achieve the image registration in a robust, semantic, and context-aware way. In this embodiment, task-specific intelligent artificial agents are trained to perform various registration tasks corresponding to anatomies being registered and the medical imaging modalities of the images being registered. For example, the task-specific intelligent artificial agents can utilize trained deep neural networks to iteratively select registration actions to implement a registration policy learned using deep reinforcement learning, or other artificial agent registration techniques described in U.S. patent application Ser. No. 15/587,094, filed May 4, 2017, entitled "Method and System for Image Registration Using an Intelligent Artificial Agent," which is incorporated herein in its entirety by reference. In addition to the individual task-specific intelligent artificial agents, an artificial registration conductor is trained. The trained artificial registration conductor is an intelligent artificial agent that automatically selects the artificial registration agent to apply, given the surgical context, the input images and the organs visible in the images. For instance, if the artificial registration conductor is given a pre-op chest CT and a DynaCT, and it knows a cardiac procedure is being performed, it will call the cardiac registration agent to perform the fusion. However, if instead a spine surgery is being done, then the artificial registration conductor agent would call the spine registration agent. The artificial registration conductor can be trained in a supervised fashion using deep learning for instance. The input to the artificial registration conductor agent is the images to be registered and meta data about the surgical context, and the output is the task-specific registration agent to call. An active learning framework can also be used, coupled with reinforcement learning, to have the conductor learn and adapt continuously as more interventions are performed.

Clinical data of various types can also be "fused" with imaging data. This could be achieved in a statistical fashion, where imaging features are combined with the clinical features in a statistical model trained in supervised way (e.g., risk scores, etc.). Alternatively, computational, multi-scale models can be employed to mechanistically integrate the information in a physiologically-plausible fashion. For example, an organ model can be built from the medical images, and the clinical data can be used to estimate the underlying physiological parameters, such as cardiac electrical conductivity, tissue elasticity, stiffness, etc. In a possible implementation, an artificial agent can be trained based on reinforcement learning to perform such a task, as described in Neumann et al., "Self-Taught Artificial Agent for Multi-physics Computational Model Personalization", *Medical Image Analysis*, Vol. 34, December 2016, pp. 52-64. Alternatively, combining the generative power of computational models, a deep learning method can be used to directly infer electrical properties from ECG signals.

Sensors (inertial measurement unit (IMU), ultra-wide band, etc.) and depth cameras (3D cameras) can be used to model an OR scene and perform image and data fusion, as well as scene understanding. More precisely, depth cameras and sensors can be used to precisely geo-localize a tool or person in the room. The localization information is thus used to associate a spatial coordinate to the object with respect to the room coordinate system. By using transformation composition, any element visualized in the image by devices can then be mapped into the room coordinate system (which can also be aligned with the patient), for comprehensive information fusion.

At step 308, real-time quantification of patient-measurements is performed. The real-time computing engine 212 of the virtual agent 210 performs real-time quantification to extract live measurements for quantitative monitoring and logging. The real-time quantification is an advantageous part of the cognitive OR system, as it is important to be able to associate quantifiable measurements/numbers to what is happening during the surgical procedure in order to understand the scene and anticipate the next steps.

Figure 4:
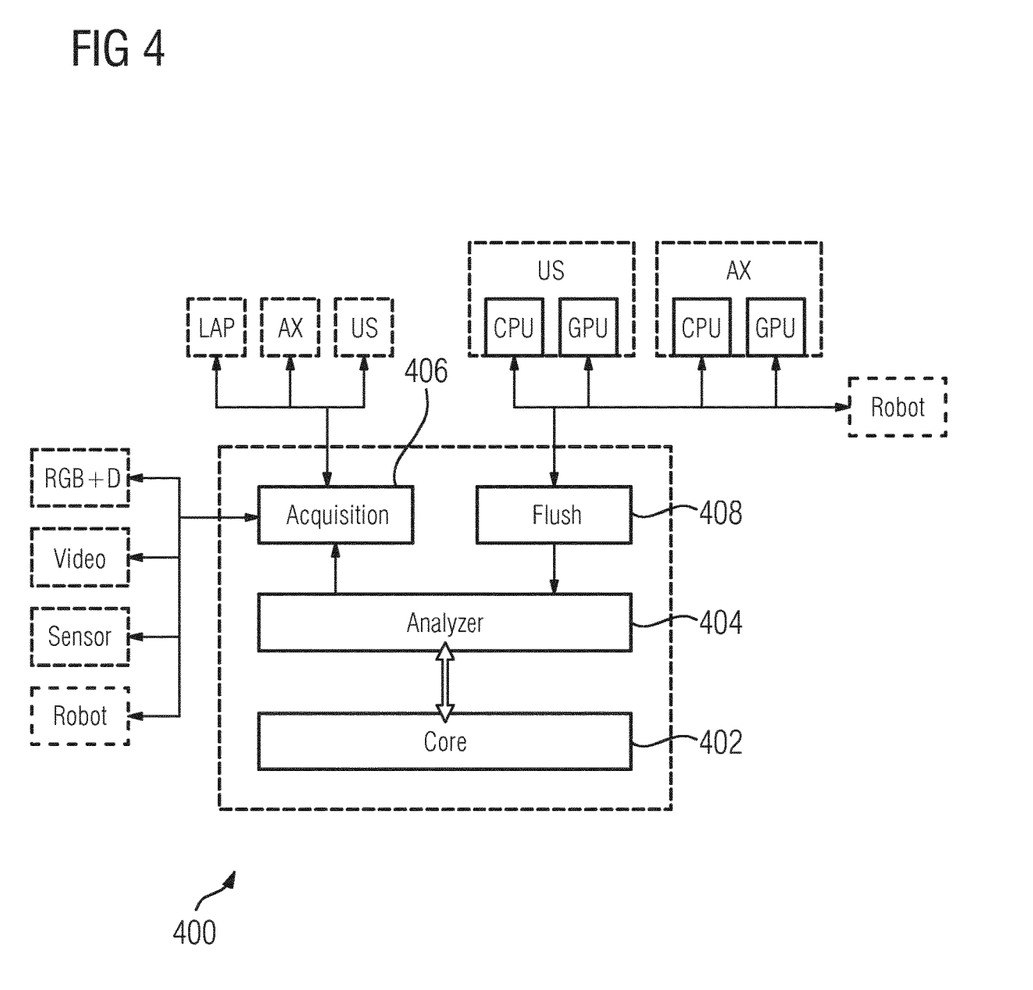
FIG. 4 illustrates a computation infrastructure for performing the real-time quantification according to an embodiment of the present invention.

FIG. 4 illustrates a computation infrastructure for performing the real-time quantification according to an embodiment of the present invention. As shown in FIG. 4, the quantification relies on a computation infrastructure 400 that is multi-threaded, lock-free, and asynchronous. The core 402 stores algorithms that are used to perform the quantification. The algorithms are executed in the analyzer 404. In an exemplary implementation, two core algorithm elements are used: robust landmark tracking and anatomical modeling (anatomical object segmentation). However, it is to be understood that additional core algorithm elements may be used as well. Robust landmark tracking includes detecting and consistently tracking landmarks in medical images and videos, or features in signals. Various landmark tracking algorithms can be used, such as those described in Voigt et al., "Robust Live Tracking of Mitral Valve Annulus for Minimally-Invasive Intervention Guidance", In *International Conference on Medical Image Computing and Computer-Assisted Intervention*, pp. 439-446, Spring International Publishing, 2015 (hereinafter "[Voigt 2015]"), and U.S. Pat. No. 9,084,531, issued Jul. 21, 2015, entitled "Providing Real-Time Marker Detection for a Stent in Medical Imaging", which are incorporated herein in their entirety by reference. According to an advantageous implementation, an artificial intelligence (AI)-based tracking method may be used to provide a robust, self-adaptive algorithm, which is beneficial for interventional applications. Live anatomy modeling, i.e., anatomical object segmentation, includes detecting and modeling/segmenting visible anatomical objects in real-time, and deriving measurements/features from the models of the anatomical objects. Various anatomical modeling/segmentation algorithms can be used. For example, [Voigt 2015] describes a detecting and tracking the mitral valve annulus on real-time ultrasound. Such a model can be similarly used, for example to monitor MitraClip positioning, device landing, etc. In an exemplary implementation, anatomy modeling relies on machine learning based segmentation and real-time tracking.

Returning to FIG. 4, acquisition 406 collects the real-time data from various real-time data streams at a current time point and inputs the data in a single input channel. For example, as shown in FIG. 4, the real-time data streams can include real-time intra-operative medical images, such as laparoscopic images (LAP), angiography x-ray images (AX), and ultrasound images (US), as well as RGD+D (red, green, blue+depth) images from a 3D camera, videos, sensor data (e.g., ECG, temperature, blood pressure, etc.), and robot data. A robot can refer to a robotic system (e.g., robotic arm) that is controllable by the virtual agent 210 or any other smart machine. The robot data can include a current state and/or position of the robot, or any other data that the robot can measure. The analyzer 404 executes robust landmark tracking algorithm elements and/or the anatomical modeling algorithm elements for the input data at the current time point to perform real-time quantitation. Flush 408 then outputs the data with the landmark tracking and/or anatomical modeling results for the current time point, so the data from the next time point can be processed by the analyzer 404. Various output data and the quantification results for that output data may be presented (e.g., via the presentation layer 214) on various output devices. For example, as shown in FIG. 4 one device is controlled to display the US images with the quantification results and another device is controlled to display the AX images with the quantification results. The robot may be controlled based on the quantification results as well by controlling actuators of the robot via the presentation layer 214.

Returning to FIGS. 2 and 3, the reasoning performed by the real-time computing engine 212 of the virtual agent 210 includes steps 310 and 312 of FIG. 3. At step 310, short-term predictions for the surgical procedure are forecast based on the current context, as well as the real-time quantification results and the fused data. Based on the fused data and the models/quantification results derived in steps 306 and 308, "fast-forward" models are employed to forecast short-term events. The fast-forward models can be implemented using computational models or statistical models. For instance, real-time computational models of organ physiology and organ-device interactions can be used to calculate the next stages of the surgical workflow, given the current context. As an example, real-time cardiac electrophysiology models, such as the electrophysiology model described in Zettinig et al., "Data-Driven Estimation of Cardiac Electrical Diffusivity from 12-lead ECG signals", *Medical Image Analysis*, Vol. 18, No. 8, 2014, pp. 1361-1376, which is incorporated herein in is entirety by reference, once personalized using EP data (preop or interventional), can be used to visualize the effect of ablation, before actually burning the tissue. A similar model can be applied for device placement, where the landing zone can be forecasted using the model. One advantage of this setup is that it is a closed loop. The forecast being ultra-short term, the model can be updated, in real-time, with data for refined predictions, in a similar fashion as weather forecast. The system can be applied also at the room level, where models can be employed to predict the trajectories of the persons in the OR for collision avoidance for instance.

At step 312, suggestions for next steps in the surgical procedure, alerts, and relevant information in the fused data are determined based on the current context, the short-term predictions, and background information, such as the patient information 204 and the information from the knowledge base of medical procedures 202. Once the virtual agent 210 performs the data fusion, real-time quantification, and forecasting of the short-term predictions, the virtual agent 210 applies an AI-based reasoning system that infers the next stages and understands the situations to raise alerts, suggests the next steps, and/or brings relevant information in the scene. Artificial intelligence and statistical learning techniques can be used to train the virtual agent 210 to effectively and autonomously perform these reasoning tasks. In an advantageous, embodiment, an artificial agent is initially trained to approach the problem as a "suggestion problem". From on a large database of previous surgical interventions, medical knowledge, guidelines, clinical trials, etc., (e.g., the medical knowledge base of medical procedures 202), the artificial agent is trained to learn distance metrics to recognize the similarity between two events. Based on the fused data, the quantification results, the short-term predictions, and the patient-data 204, the trained artificial agent can then determine one or more events in the knowledge base of medical procedures 202 that is/are most similar to the current context and then infer the next steps of the surgical procedure to suggest (and/or whether to raise an alert or what information should be identified as relevant) based on the similar event or events in the knowledge base of medical procedures 202. Reinforcement learning methods can then be applied to adapt the model to a specific user. In this case, the artificial agent receives a positive reward if the agent performs the task it forecasted/suggested, negative reward otherwise. The Q-function can be approximated by a deep reinforcement learning architecture coupled with memory systems (short term, using LSTM architectures, but also longer terms, using derivable memory architectures), where the input are the data streams, and the output the suggested task. To formally describe the surgical scene, surgical ontologies can be used.

At step 314, the virtual agent 210 interacts with the operators and the OR environment via the presentation layer 214 to present the suggested next steps of the surgical procedure, any alerts determined to be raised, and the relevant information from the data sources. The virtual agent 210 uses the adaptive presentation layer 214 to interact with the surgeons/operators and any other actors in the OR (human or robotics). The presentation layer 214 controls images and data to be consistently displayed on a screen. For example, the presentation layer 214 can utilize hyper-realistic rendering to visualize the medical images and other data, including the results of the data fusion and the real-time quantification. When the virtual agent 210 determines what information from the images and other data is most relevant based on the current context and the suggested next step of the surgical procedure, the presentation layer 214 can control only the most relevant information in the images and other data to be displayed. Instructions for the suggested next step can also be displayed on the screen, as well as a visual indication of any alerts (e.g., alerts regarding patient safety or an alert regarding an imminent collision in the OR).

In an exemplary embodiment, the virtual agent 210 can interact like a virtual assistant, through natural language using a synthetic voice. In this case, the virtual agent 210 can answer questions (using the real-time reasoning based on the real-time data fusion and quantification), automatically present the relevant information according to the reasoning system, etc. The synthetic voice of the virtual agent 210 can be accessible to everyone in the OR, or just to the surgeon (e.g., via an earphone or bone conduction). In a possible implementation, in addition to the synthetic voice, the virtual agent 210 can also be visualized using augmented reality, like a hologram. In another possible embodiment, augmented reality could also be used to visualize the suggested next steps of the surgical procedure.

In another advantageous embodiment, the virtual agent 210 can perform autonomous actions related to the surgical procedure corresponding to the suggested next steps, for example by directly controlling other devices in the OR. In particular, the presentation layer 214 of the virtual agent 210 can be connected to actuators (robotics, devices, etc.) to directly perform a certain task in the OR. For example, the virtual agent 210 can automatically order devices, decide and adjust drug levels, control anesthesia, etc. In addition, the virtual agent 210 can connect to actuators of an image scanner, such as a C-arm image acquisition device, to adjust settings, such as the angulation of the C-arm image acquisition device, to automatically control the intra-operative image acquisition. To cope with the lack of a unified interface, a modular, pluggable system can be used, in which devices are interfaced through "drivers" that translate the device data stream into a common internal data representation and management.

The method of FIG. 3 can be repeated for the duration of the surgical procedure to provide automated real-time assistance from the virtual agent 210 over the whole surgical procedure.

Figure 5:
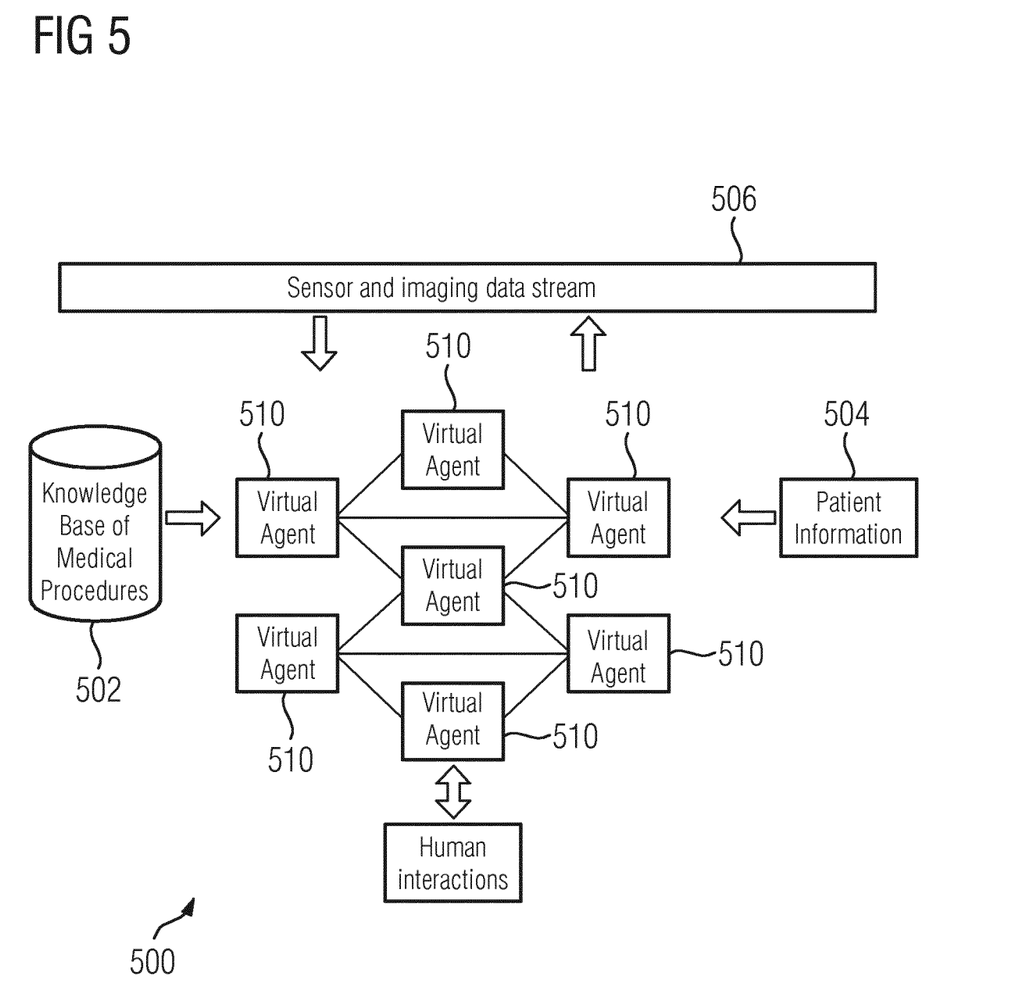
FIG. 5 illustrates a distributed multi-agent system for providing automated AI-based assistance for a surgical procedure according to an embodiment of the present invention.

The above identified intelligent agent system of FIG. 2 can be extended to multiple virtual agents, communicating between each. FIG. 5 illustrates a distributed multi-agent system for providing automated AI-based assistance for a surgical procedure according to an embodiment of the present invention. As shown in FIG. 5, the system 500 includes multiple virtual agents 510. Each of the virtual agents 510 receives data from the sensor and imaging data stream 506, inputs patient information 504 and information from the knowledge base of medical procedures 502, and operates similarly to the virtual agent 210 of FIG. 2 described above. However, the various virtual agents 510 can be trained for specific tasks corresponding to specific portions of the intervention workflow, and the virtual agents 510 communicate with each other to share relevant information, suggestions, alerts, etc., which increases the information available to each virtual agent 510. Accordingly, the use of multiple virtual agents provides advantages in that each virtual agent can be trained on specific tasks, and more enhances intelligence can emerge from the multi-agent system. In an advantageous implementation, the virtual agents can be distributed throughout the entire interventional workflow. For example, a virtual agent can be in the hospital room, monitoring and acquiring data before the intervention. This virtual agent could help identify risks and adverse events. Another virtual agent can be located in the OR, as previously described above in FIG. 2. Another virtual agent can be located in the ICU monitoring and acquiring data during recovery. These three virtual agents communicate to share information between them. For instance, the ICU virtual agent would know what happened in the past and adapt, if necessary, the suggestions/recommendations accordingly.

In various embodiments, the above described intelligent artificial agent systems and methods can be applied to various different applications. Example applications for the above described intelligent artificial agent system are described herein, but it is to be understood that the present invention is not limited to only these specific applications and may be similarly extended to other applications as well.

In an exemplary embodiment, the above described intelligent artificial agent system may be applied for intelligent room and environment control, including providing a centralized alert system and environmental control, live dose and sterility monitoring for patients and operators with an alert system, automatic ordering of tool availability and device preparation based on current context, and/or automatic OR music playlist based on current context.

In an exemplary embodiment, the above described intelligent artificial agent system may be applied for smart scanning and workflow automation, including automatic adaptation of imaging scanners and devices to the current context for imaging acquisition (predictive scanning), including automatic selection of imaging modality and parameters, In an exemplary embodiment, the above described intelligent artificial agent system may be applied for intelligent patient management and therapy delivery. The intelligent artificial agent system can provide therapy recommendations by using modeling to virtually test different therapies and provide procedural recommendations. The intelligent artificial agent system can be used for a body-GPS application, in which given an intervention type, the intelligent artificial agent can automatically perform preparation for the intervention (take pre-op image, segment it, path planning, fusion, etc.), and provide navigational information (visual cues, audio cues, etc.). The intelligent artificial agent system can be used for automatic check list and verification (pre-operative, intra-operative, and post-operative), including tool and disposable tracking. The intelligent artificial agent system can be used to provide a connection to a pathologist and diagnostics, with a centralized reporting system. The intelligent artificial agent system can be used to provide a surgical/interventional error alert system. The intelligent artificial agent system can be used to generate predictors for bleeding and other life-threatening events through imaging, cameras, and vitals measurements. The intelligent artificial agent system can be used to provide drug administration suggestions based on the current context, physiological measurements, and medical history of the patient. The intelligent artificial agent system can be used for end-to-end automatic fusion of images, in which based on context or user-selected pre-op imaging, therapy stage, etc., images are robustly fused to bring the relevant information at the appropriate time. The intelligent artificial agent system can be used to provide automatic identification for humans, in which based on the fused images, labeling of what is being seen in the scene is provided. The intelligent artificial agent system can be used to control actuators (e.g., robotic systems, probes, etc.) as a "third arm" to assist the surgeon, including robotic scrub nurse.

Figure 6:
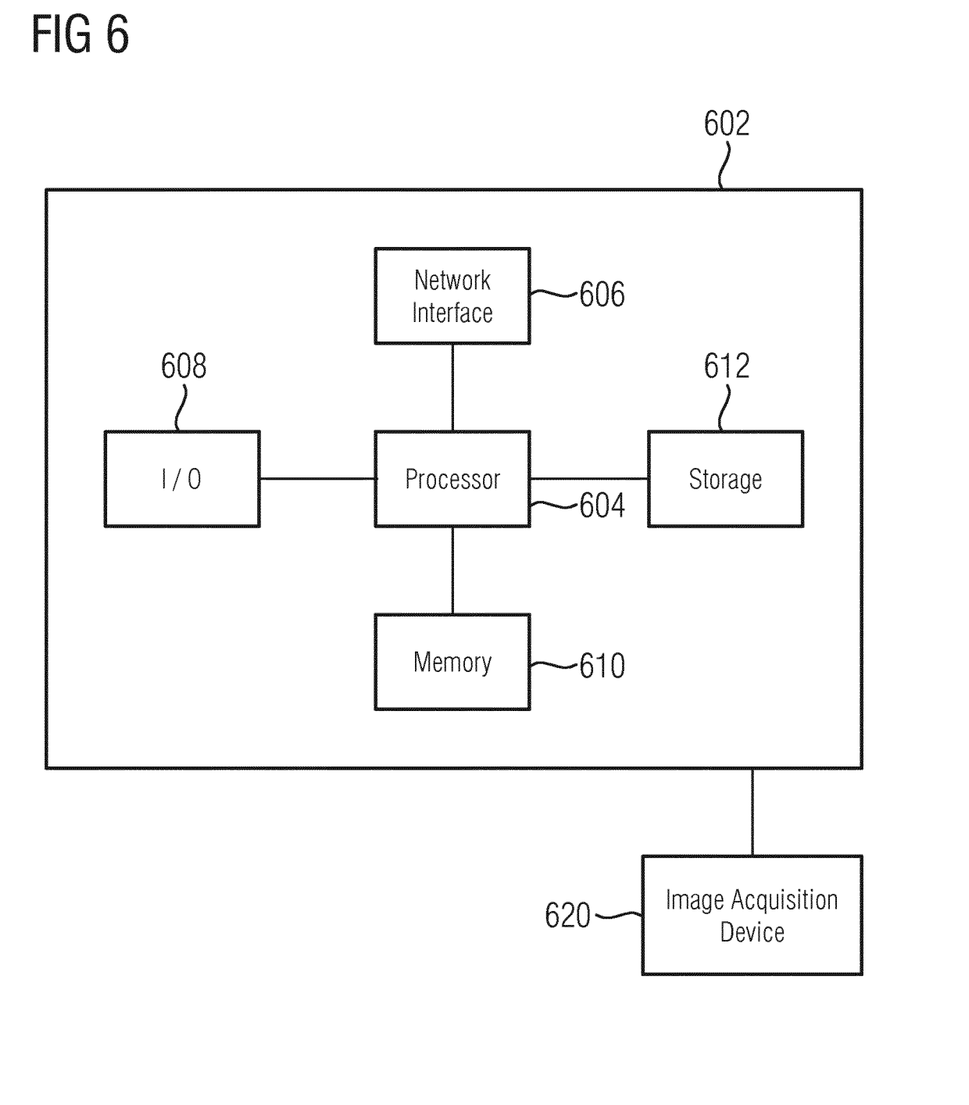
FIG. 6 is a high-level block diagram of a computer capable of implementing the present invention.

The above-described method for providing an intelligent artificial agent based support for a surgical procedure can be implemented on one or more computers using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the method of FIG. 3 may be defined by the computer program instructions stored in the memory 610 and/or storage 612 and controlled by the processor 604 executing the computer program instructions. One or more image acquisition device(s) 620, such as a CT scanning device, C-arm image acquisition device, MR scanning device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). One skilled in the art will recognize that an implementation of an actual computer could contain other components as well, and that FIG. 6 is a high level representation of some of the components of such a computer for illustrative purposes.

In one embodiment, the computer that performs all of a subset of the method steps of the above-described method for providing an intelligent artificial agent based support for a surgical procedure may be implemented in network-based cloud computing system. In such a network-based cloud computing system, a server communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer (s). The server may also transmit data adapted to cause a client computer to perform a specified function, e.g., to perform a calculation, to display specified data on a screen, etc. Certain steps of the above described methods may be performed by a server or by other computers/processors in the network-based cloud-computing system. Certain steps of the above described methods may be performed locally by a client computer in a network-based cloud computing system. The steps of the above described methods may be performed by one or more devices in the network-based cloud-computing system or by a local client computer in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for providing automated computer-based assistance for a surgical procedure, comprising:
fusing data related to the surgical procedure from multiple data sources based on a current context, wherein the data includes medical images of a patient acquired using one or more medical imaging modalities;
performing real-time quantification of patient measurements based on the data from the multiple data sources based on the current context;
forecasting short-term predictions in the surgical procedure based on the current context, the fused data, and the real-time quantification of the patient measurements;
determining suggestions for next steps in the surgical procedure and relevant information in the fused data based on the current context and the short-term predictions; and
presenting the suggestions for the next steps and the relevant information in the fused data to an operator.

2. The method of claim 1, wherein the data includes medical images acquired using multiple different medical imaging modalities and fusing data related to the surgical procedure from multiple data sources based on a current context comprises:
registering the medical images acquired using the multiple different medical imaging modalities.

3. The method of claim 2, wherein registering the medical images acquired using the multiple different medical imaging modalities comprises:
selecting, by a trained artificial registration conductor, a trained artificial registration agent based on the different medical imaging modalities of the medical images and a current surgical context; and
registering the medical images acquired using the multiple different medical imaging modalities using the selected trained artificial registration conductor.

4. The method of claim 1, wherein the data further includes clinical measurements of the patient and fusing data related to the surgical procedure from multiple data sources based on a current context comprises:
fusing the clinical measurements of the patient with the medical images of the patient.

5. The method of claim 1, wherein performing real-time quantification of patient measurements based on the data from the multiple data sources based on the current context comprises:
performing at least one of landmark tracking or anatomical object segmentation in the medical images of the patient.

6. The method of claim 5, wherein performing at least one of landmark tracking or anatomical object segmentation in the medical images of the patient comprises:
selecting a landmark tracking algorithm or an anatomical object segmentation algorithm from a plurality of stored core algorithms for landmark tracking or anatomical object segmentation based on the current context; and
performing real-time landmark tracking or anatomical object segmentation in the medical images of the patient using the selected landmark tracking or anatomical object segmentation algorithm.

7. The method of claim 1, wherein forecasting short-term predictions in the surgical procedure based on the current context, the fused data, and the real-time quantification of the patient measurements comprises:
forecasting the short-term predictions in the surgical procedure based on the current context, the fused data, and the real-time quantification of the patient measurements using fast-forward models, wherein the fast-forward models include at least one of computational models or statistical models.

8. The method of claim 7, further comprising:
updating the fast-forward models is real-time based on newly received data and refining the short-term predictions based on the updated fast-forward models.

9. The method of claim 1, wherein determining suggestions for next steps in the surgical procedure and relevant information in the fused data based on the current context and the short-term predictions comprises:

determining suggestions using a trained intelligent artificial agent that is trained to learn distance metrics to recognize a similarity between the current context and events in a knowledge base of medical procedures and infer suggestions for the next steps based on the events recognized to be similar to the current context in the knowledge base of medical procedures.

10. The method of claim 9, wherein the trained artificial agent is adapted to a specific user using a deep reinforcement learning method that rewards suggested next steps that performed by the specific user.

11. The method of claim 1, wherein determining suggestions for next steps in the surgical procedure and relevant information in the fused data based on the current context and the short-term predictions comprises:
determining whether to raise an alert based on the current context and the short-term predictions.

12. The method of claim 11, further comprising:
providing at least one of an audio alert or a visual result in response to a determination to raise an alert based on the current context and the short-term predictions.

13. The method of claim 1, wherein presenting the suggestions for the next steps and the relevant information in the fused data to an operator comprises:
displaying only the relevant information in the fused data.

14. The method of claim 1, wherein presenting the suggestions for the next steps and the relevant information in the fused data to an operator comprises:
presenting the suggestions for the next steps and the relevant information to the operator through natural language using a synthetic voice.

15. The method of claim 1, wherein presenting the suggestions for the next steps and the relevant information in the fused data to an operator comprises:
visualizing relevant information and guiding the suggested next steps using augmented reality.

16. The method of claim 1, further comprising:
automatically controlling a device in an operating room to perform a task in the surgical procedure based on the determined suggestions for the next steps.

17. An apparatus for providing automated computer-based assistance for a surgical procedure, comprising:
means for fusing data related to the surgical procedure from multiple data sources based on a current context, wherein the data includes medical images of a patient acquired using one or more medical imaging modalities;
means for performing real-time quantification of patient measurements based on the data from the multiple data sources based on the current context;
means for forecasting short-term predictions in the surgical procedure based on the current context, the fused data, and the real-time quantification of the patient measurements;
means for determining suggestions for next steps in the surgical procedure and relevant information in the fused data based on the current context and the short-term predictions; and
means for presenting the suggestions for the next steps and the relevant information in the fused data to an operator.

18. The apparatus of claim 17, wherein the data includes medical images acquired using multiple different medical imaging modalities and the means for fusing data related to the surgical procedure from multiple data sources based on a current context comprises:
means for registering the medical images acquired using the multiple different medical imaging modalities.

19. The apparatus of claim 17, wherein the data further includes clinical measurements of the patient and fusing data related to the surgical procedure from multiple data sources based on a current context comprises:
means for fusing the clinical measurements of the patient with the medical images of the patient.

20. The apparatus of claim 17, wherein the means for performing real-time quantification of patient measurements based on the data from the multiple data sources based on the current context comprises:
means for performing at least one of landmark tracking or anatomical object segmentation in the medical images of the patient.

21. The apparatus of claim 17, wherein the means for forecasting short-term predictions in the surgical procedure based on the current context, the fused data, and the real-time quantification of the patient measurements comprises:
means for forecasting the short-term predictions in the surgical procedure based on the current context, the fused data, and the real-time quantification of the patient measurements using fast-forward models, wherein the fast-forward models include at least one of computational models or statistical models.

22. The apparatus of claim 17, wherein the means for determining suggestions for next steps in the surgical procedure and relevant information in the fused data based on the current context and the short-term predictions comprises:
means for determining suggestions using a trained intelligent artificial agent that is trained to learn distance metrics to recognize a similarity between the current context and events in a knowledge base of medical procedures and infer suggestions for the next steps based on the events recognized to be similar to the current context in the knowledge base of medical procedures.

23. The apparatus of claim 22, wherein the trained artificial agent is adapted to a specific user using a deep reinforcement learning method that rewards suggested next steps that performed by the specific user.

24. The apparatus of claim 17, wherein the means for determining suggestions for next steps in the surgical procedure and relevant information in the fused data based on the current context and the short-term predictions comprises:
means for determining whether to raise an alert based on the current context and the short-term predictions.

25. The apparatus of claim 24, further comprising:
means for providing at least one of an audio alert or a visual result in response to a determination to raise an alert based on the current context and the short-term predictions.

26. The apparatus of claim 17, further comprising:
means for automatically controlling a device in an operating room to perform a task in the surgical procedure based on the determined suggestions for the next steps.

* * * * *